United States Patent [19]

Wang et al.

[11] Patent Number: 4,968,812

[45] Date of Patent: Nov. 6, 1990

[54] SPIROLACTONELACTAMS

[75] Inventors: Pen-Chung Wang; William J. Asbell, both of Houston, Tex.

[73] Assignee: Shell Oil Company, Houston, Tex.

[21] Appl. No.: 370,508

[22] Filed: Jun. 23, 1989

[51] Int. Cl.$^5$ ............................................. C07D 519/00
[52] U.S. Cl. ........................................ 548/410; 544/6; 544/70; 544/230; 546/15
[58] Field of Search .............. 548/410; 546/15; 544/6, 544/70, 230

[56]  References Cited

U.S. PATENT DOCUMENTS

| | | | |
|---|---|---|---|
| 2,149,678 | 3/1939 | Hovey et al. | 260/2 |
| 2,195,570 | 4/1940 | Hovey et al. | 260/65 |
| 2,279,752 | 4/1942 | Jacobson | 260/78 |
| 2,987,502 | 6/1960 | Ferstandig et al. | 260/63 |
| 3,408,334 | 10/1968 | Caldwell et al. | 260/78 |
| 3,637,602 | 1/1972 | Conciatori | 260/78 |
| 4,064,086 | 12/1977 | Cowsar et al. | 260/29.2 R |
| 4,847,388 | 7/1989 | Wang | 548/410 |
| 4,885,351 | 12/1989 | Wang | 548/409 |
| 4,886,863 | 12/1989 | Wang | 548/409 |
| 4,888,408 | 12/1989 | Wang | 528/323 |

FOREIGN PATENT DOCUMENTS 43-22651  9/1968  Japan .

OTHER PUBLICATIONS

Hachikama et al., *J. Soc. Chem. Ind. Japan,* 45, p. 706 (1942).
Hachikama et al., *J. Soc. Chem. Ind. Japan,* 46, p. 119B (1943).
Kobayashi et al., *Sen-i Gackaishi,* 14, pp. 881–891 (1958).
Schroeder, E., *Plaste u. Kautschuk,* 5, pp. 49–54 (1958).
Schroeder, E., *Plaste u. Kautschuk,* 8, pp. 121–124 (1961).
Pariza et al, "Synthetic Communications", 13(3), pp. 243–254 (1983).
Cowsar et al, ACS Meeting, Abstract (Los Angeles 1988) pp. 521–525.

*Primary Examiner*—Mark L. Berch

[57]  ABSTRACT

A novel class of bis(spirolactonelactam) compounds is produced by reaction of a primary diamine in the presence of a stoichiometric excess of a spirodilactam precursor selected from ketodiacid compounds and 1,6-dioxo [4.4] spirodilactones.

10 Claims, No Drawings

SPIROLACTONELACTAMS

FIELD OF THE INVENTION

This invention relates to a certain class of spirolactonelactams. More particularly, the invention relates to compounds containing two moieties of a 1-aza-6-oxospiro [4.4] spirolactonelactam wherein the spirolactonelactam moieties are connected to the remainder of the molecule through the nitrogen of the spiro ring.

BACKGROUND OF THE INVENTION

The reaction of diamines and difunctional acidic materials is well known in the art to produce polyamide polymers. A commercial example of the production of such polymers is the illustrative reaction of hexamethylenediamine adipic acid to produce the polyamide known as NYLON ® 66. The nature of the polyamide product will vary, depending in part on the nature of the acid compound and the amine.

The reaction of a ketobenzoic acid, i.e., benzoylbenzoic acid, and diamines is shown by Hovey et al, U.S. Pat. Nos. 2,149,678 and 2,195,570. The reaction of aromatic dicarboxylic acids and photosensitive diamines is shown by Nakama et al, U.S. Pat. No. 4,595,745. Caldwell et al, U.S. Pat. No. 3,408,334, describe the reaction of dicarboxylic acids and diamines in the presence of a tin compound as catalyst. Reaction of α,β-unsaturated carboxylic acids and primary and secondary diamines is disclosed by Conciatori, U.S. Pat. No. 3,637,602. The use of a dicarboxylic acid of additional functionality, e.g., 4-oxoheptanedioic acid, in the production of polymers is shown by Ferstandig, U.S. Pat. No. 2,987,502, but the reaction was with a polyhydric alcohol and the product was a polyester. The reaction of this type of acid with diamines is shown by Jacobson, U.S. Pat. No. 2,279,752.

A class of compounds that function in many ways similar to dicarboxylic acids is the class of 1,6-dioxa [4.4] spirodilactones. The simplest member of the class, 1,6-dioxaspiro[4.4]nonane-2,7-dione, is known and has been prepared, among other procedures, by the method of Pariza et al, *Synthetic Communications*, Vol. 13(3), pp. 243-254 (1983). These spirodilactones have demonstrated utility as curing agents to produce compositions which do not shrink upon curing. This property probably results from opening of the spirodilactone ring system during the curing process, Knowles et al, J. Appl. Polymer Science, Vol. 10(6), pp. 887-889 (1966). It is generally characteristic of the spirodilactone ring system that it tends to produce ring-opened products as further evidenced by the above Pariza et al article and Cowsar et al, U.S. Pat. No. 4,064,086.

There are some processes in which the spiro ring system of a spirodilactone reactant is retained in part or in total. Cowsar et al, "Biodegradable Polyamides Based on 4,4'-Spirobibutyrolactone", ACS Meeting Abstract (Los Angeles, 1988), pages 521-525, describe a terpolymer prepared from reaction of a spirodilactone and diamine in which some units retain a spiro structure and others do not. U.S. Pat. No. 4,889,907 and allowed and Ser. No. 245,618 filed Sept. 16, 1988, describe and claim a process in which spirodilactones react with hydroxy-containing primary amines to produce monomeric substituted spirolactonelactams or spirodilactams. A copending U.S. patent application Ser. No. 314,513, filed Feb. 23, 1989, describes and claims certain monomeric products produced by reaction of two molecules of a primary diamine and one molecule of a spirodilactam precursor selected from ketodicarboxylic acid compounds or spirodilactones.

A copending U.S. patent application Ser. No. 254,432, filed Sept. 16, 1988 describes and claims certain polyamide polymers containing 1,6-diazo [4.4] sirodilactam moieties as well as the process of their production by reaction of primary diamines and a spirodilactam precursor as above defined. Such polymers are linear alternating polymers wherein moieties derived from the diamine alternate with spirodilactam moieties. By conducting this polymerization reaction with a mixture of primary diamines, it is possible to produce a linear alternating polymer wherein the alternate diamine moieties are a random mixture of the diamines in the mixed diamine reactant. It would be of advantage, however, to provide a process for the production of such polyamide polymers wherein moieties derived from a primary diamine alternate with spirodilactam moieties derived from two different primary diamines also alternate within the polymeric chain. Such a polymer is produced through isolation of an intermediate in the polymer production process and subsequent reaction with dissimilar diamine.

BACKGROUND OF THE INVENTION

The present invention provides a process for the production of a novel class of spirolactonelactams. More particularly, the invention provides for contacting a primary diamine with a stoichiometric excess of a spirolactam precursor selected from 4-oxoheptanedioic acid compounds or 1,6-dioxo [4.4] spirodilactones. The resulting initial product is cyclized to a bis(spirolactonelactam) compound.

DESCRIPTION OF THE INVENTION

The bis(spirolactonelactam) compounds of the invention are produced by initially contacting a primary diamine, i.e., an organic compound having two primary amino groups (—NH$_2$ groups) with a spirolactonelactam precursor of up to 30 carbon atoms inclusive selected from ketodiacid compounds and 1,6-dioxo [4.4] spirodilactones. In one embodiment, the spirolactonelactam precursor is a ketodicarboxylic acid compound having two carbon atoms between the keto group and each carboxy function. In other terms, the ketodicarboxylic acid compound is a 4-oxoheptanedioic acid compound. Although a variety of such ketodiacid compounds having a variety of substituents in addition to the keto and carboxy functions are satisfactory, the preferred 4-oxoheptanedioic acid compounds are represented by the formula

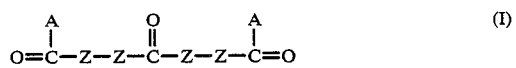

$$O=\overset{A}{\underset{|}{C}}-Z-Z-\overset{O}{\underset{\|}{C}}-Z-Z-\overset{A}{\underset{|}{C}}=O \quad (I)$$

wherein A independently is hydrogen, alkoxy, preferably lower alkoxy of up to 4 carbon atoms inclusive, or halo, preferably the middle halogens chloro or bromo. In formula I, Z independently is <C(Z')$_2$ in which Z' independently is hydrogen, alkyl, preferably lower alkyl of up to 4 carbon atoms atoms inclusive, halo, preferably the lower halogens fluoro or chloro, or aryl, preferably phenyl, or Z is such that two adjacent Z moieties form a ring system Z" of from 5 to 7 ring atoms, up to two of which are heteroatoms selected from nitrogen, oxygen or sulfur with the remainder of the ring atoms being carbon atoms, there being up to 15 carbon atoms in each Z'', two of which form a bridge between the carbon atoms connected by the adjacent Z moieties. The Z moieties are hydrocarbyl containing only atoms of carbon and hydrogen or are substituted-hydrocarbyl containing additional atoms such as halogen in the form of inert, monovalent carbon-atom substituents. When adjacent Z moieties form Z'', the ring system is aromatic, cycloaliphatic or heterocyclic.

In one embodiment employing the ketodiacid as spirolactonelactam precursor, each Z moiety is acyclic, i.e., Z is not a part of a fused ring substituent and is >C(Z')₂. The ketodiacid compound is therefore an acyclic 4-oxoheptanedioic acid compound such as those represented by the formula

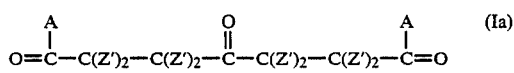

wherein A and Z' have the previously stated meanings. Such 4-oxoheptanedioic acid compounds include 4-oxoheptanedioic acid, dimethyl 4-oxoheptanedioate, 2,6-dimethyl-4-oxoheptanedioic acid, 2,3,5,6-tetramethyl-4-oxoheptanedioyl chloride, di-n-propyl 2,6-diphenyl-4-oxoheptanedioate, 3,5-di-n-butyl-4-oxoheptanedioic acid and 6-carbomethoxy-3,3,5,5-tetramethyl-4-oxohexanoic acid. The preferred compounds of the above formula Ia are those wherein each Z' is hydrogen or methyl, especially those compounds wherein at least one Z' of each Z'-substituted carbon atom is hydrogen. The term A is preferably hydroxy or methoxy, especially hydroxy. These ketodiacid compounds are known compounds or are produced by known methods. A preferred method of producing diesters of the above formula, i.e., A is alkoxy, is by the process of reacting formaldehyde and an unsaturated ester such as is described in U.S. Pat. No. 4,800,231. Conversion of the esters thereby produced to corresponding free acids or acid halides is by known methods.

In a second embodiment of the ketodiacid compound as spirolactonelactam precursor, the 4-ketodiacid incorporates cyclic moieties between the keto group and each carboxy function, i.e., each pair of adjacent Z moieties forms a ring system Z''. Such diacid compounds are represented by the formula

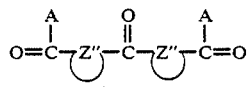

wherein Z'' has the previously stated meaning. Illustrative of these cyclic ketodiacids are di(2-carboxycyclohexyl) ketone, di(2-carboxyphenyl) ketone, di(2-carboxypropoxycyclo-4-pentenyl) ketone, di(3-chlorocarbonylphenyl) ketone, di(2-carboxypyridyl) ketone, 2-carboxyphenyl N-methyl-3-carboxy-2-pyrryl ketone, di(3-carbomethoxy-2-naphthyl) ketone and di(3-carbomethoxy2-morpholyl) ketone. The preferred cyclic ketodiacid compounds of formula Ib are those wherein each Z'' is a ring system of from 5 to 6 atoms inclusive and up to one nitrogen heteroatom. Such dicyclic 4-ketodiacid compounds are known compounds or are produced by known methods, for example, the method of U.S. Pat. No. 1,999,308, or by the process of Cava et al, J. Am. Chem. Soc., 20, 6022 (1955).

In yet another modification of the 4-ketodiacid compound as the spirolactonelactam precursor, the 4-ketodiacid incorporates one cyclic moiety, Z'', with the remainder of the Z moieties being acyclic, i.e., the compounds represented by the formula

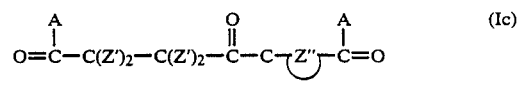

wherein A, Z' and Z'' have the previously stated meanings. Such ketodiacids of one cyclic moiety are illustrated by 3-(2-carboxybenzoyl)-propionic acid, ethyl 3-(3-carbomethoxy-2-pyridyloyl)-2-ethylpropionate and 3-(2-carboxy-4-methylbenzoyl)butyrl chloride. The ketodiacids of the above formula Ic are known compounds or are produced by known methods. For example, 2-carboxymethylbenzaldehyde reacts with methyl acrylate according to the general teachings of U.S. Pat. No. 4,800,231 to produce methyl 3-(2-carbomethoxybenzoyl)propionate.

In a second embodiment of the invention, the spirolactonelactam precursor is a 1,6-dioxospiro[4.4]nonane-2,7-dione compound wherein the spiro ring carbon atoms are substituted with monovalent substituents or the spiro ring incorporates fused cyclic substituents which include the 3- and 4- ring positions and/or the 8- and 9- ring positions. One class of such [4.4] spirodilactones is represented by the formula

wherein Z has the previously stated significance. In a first modification of the spirodilactones as spirolactonelactam precursors, the Z moieties are acyclic, i.e., Z is C(Z')₂, and the spirodilactone is represented by the formula

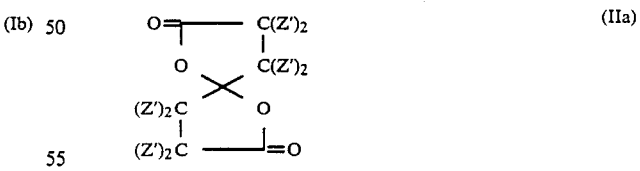

wherein Z' has the previously stated meaning. Illustrative of such spirodilactones are 1,6-dioxaspiro[4.4]nonane-2,7-dione, 3,8-dimethyl-1,6-dioxaspiro[4.4]nonane-2,7-dione, 3,4,8,9-tetramethyl-1,6-dioxaspiro[4.4]-nonane-2,7-dione, 4,9-diphenyl-1,6-dioxaspiro[4.4]nonane-2,7-dione, 3,3,4,-4,8,8,9,9-octamethyl-1,6-dioxaspiro[4.4]nonane-2,7-dione and 3,4,8,9-tetrafluro- 1,6-dioxaspiro[4.4]nonane-2,7-dione. The preferred spirodilactones of the above formula IIa are those wherein at least one Z', and preferably each Z', of a Z'-substituted ring carbon atom is hydrogen. The compounds of formula IIa are known compounds or are produced by known methods such as the process of the above Pariza et al reference.

In the modification of the spirodilactones as spirolactonelactam precursor which incorporates a cyclic moiety as a fused ring substituent of each of the two spiro rings, the spirodilactones are represented by the formula

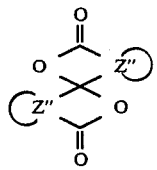
(IIb)

wherein Z" has the previously stated meaning. Typical compounds of this formula IIb are 3,4,8,9-dibenzo-1,6-dioxaspiro[4.4]nonane-2,7-dione, 3,4,8,9-di(cyclopentano)-1,6-dioxaspiro[4.4]nonane-2,7-dione, 3,4,8,9-di(4-methylbenzo)-1,6-dioxaspiro[4.4]nonane-2,7-dione and 3,4,8,9-di(pyrido)-1,6-dioxaspiro[4.4]nonane-2,7-dione. These compounds are known compounds or are produced by known methods, for example, the process of the above Cava et al article or the method of U.S. Pat. No. 1,999,308.

In the third modification of the spirodilactone as spirolactonelactam precursor, a cyclic moiety is fused to one spiro ring and the other spiro ring is free from fused ring substituents. Such spirodilactones are represented by the formula

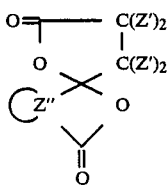
(IIc)

wherein Z' and Z" have the previously stated significance. Such spirodilactones are illustrated by 3-methyl-8,9-benzo-1,6-dioxaspiro[4.4-nonane-2,7-dione, 3,4-pyrido-1,6-dioxaspiro[4.4]nonane-2,7-dione and 3,4-morpholo-1,6-dioxaspiro[4.4]nonane-2,7-dione. The spirodilactones of formula IIc are produced by known methods such a the dehydration of the corresponding ketodiacid. By way of specific illustration, 3,4-benzo-1,6-dioxaspiro[4.4]nonane-2,7-dione is produced by dehydration of 3-(2-carboxybenzoyl)propionic acid through application of heat.

The preferred spirodilactone precursors of the spirolactonelactams are those which are hydrocarbyl except for the lactone oxygen atoms. Particularly preferred are the spirodilactones which are free from fused ring substituents (formula IIa) or which have a fused ring substituent on each spiro ring (formula IIb). An especially preferred member of the first class is 1,6-dioxaspiro[4.4-]nonane-2,7-dione while an especially preferred member of the latter class is 3,4,8,9-dibenzo-1,6-dioxaspiro[4.4]nonane-2,7-dione.

The spirolactonelactam precursor is reacted according to the invention with a primary diamine, that is, an organic compound having two primary amino groups, i.e., —NH$_2$ groups, as carbon atom substituents. While the reaction to produce the spirolactonelactam products of the invention will take place with a variety of primary diamines having a variety of structures, best results are obtained if the two primary amino groups are not located on adjacent carbon atoms, that is, at least one atom separates the carbon atoms on which the primary amino groups are substituents. One class of such primary diamines comprises diamines of up to 30 carbon atoms which are represented by the formula

$$H_2N-R-NH_2 \qquad (III)$$

wherein R is a divalent organic radical of up to 30 carbon atoms selected from divalent alkylene or divalent arylene of from 1 to 2 aromatic rings inclusive, which, when two rings are present, incorporates rings which are fused, connected by a direct valence bond or connected by alkylene of up to 8 carbon atoms inclusive, oxy, thio, sulfonyl, carbonyl, dioxyphenylene, 2,2-di(oxyphenyl)propane, di(oxyphenyl) sulfone or dioxydiphenylene, with the proviso that the two amino substituents are not located on adjacent carbon atoms. R is otherwise hydrocarbyl containing only atoms of carbon and hydrogen besides any other atoms present in connecting groups when two aromatic rings are present, or R is substituted hydrocarbyl containing additional atoms as inert, monovalent carbon atom substituents, e.g., halogen atoms, preferably middle halogens chloro or bromo.

Illustrative of alkylene-containing diamines of the above formula III are trimethylenediamine, tetramethylenediamine, hexamethylenediamine, octamethylenediamine, 1,7-diamino-4-methyloctane, 1,4-diaminocyclohexane, di(4-aminocyclohexyl)methane, dodecamethylenediamine and 1,6-diamino-3,4-diethylhexane. Arylene diamines of the above formula IV include 1,4-phenylenediamine, 2,4-toluenediamine, 4,4'-diaminobiphenyl, 1,5-diaminonaphthalene, di(3-aminophenyl) ether, di(4-aminophenyl)methane, 2,2-di(3-amino-4-methylphenyl)propane, di(4-amino-2-ethylphenyl) sulfone, di(4-amino-3-chlorophenyl) ketone, di(2-aminophenyl) sulfide, 1,3-di(3-aminophenyloxy)benzene, 2,2-di[4-(4-aminophenyloxy)phenyl]propane and 4,4'-di(4-aminophenyloxy)biphenyl. The preferred primary diamines of the above formula III are those wherein R is divalent arylene and is hydrocarbyl except for any other atoms of connecting groups within R when two aromatic rings are present. Particularly preferred are the di(aminophenyl)alkanes, especially the di(4-aminophenyl)alkanes such as di(4-aminophenyl)methane.

In the reaction mixture the spirolactonelactam precursor is employed in stoichiometric excess over the primary diamine. Stoichiometric considerations would indicate that two moles of spirolactonelactam precursor react with one mole of primary diamine. Suitable molar reactant ratios of spirolactonelactam precursor to primary amine should be from about 2.1:1 to about 8:1 or even higher, but preferred molar reactant ratios are from about 2.2:1 to about 4:1. The reaction is conducted at an elevated temperature in the liquid phase in the presence of a reaction diluent. Diluents which are inert to the reactants and product and are capable of dissolving at least a portion of each reactant at reaction temperature are satisfactory. Suitable diluents include ketones such as methyl isobutyl ketone and di-isopropyl ketone, esters such as ethyl 2-ethyhexanoate, ethers including acyclic ethers such as diethylene glycol dimethyl ether and tetraethylene glycol dimethyl ether as well as cyclic ethers such as tetrahydroiuran and dioxane, N-alkylamides such as N,N-dimethylacetamide and N-methyl-2-pyrrolidone.

The reaction of the spirolactonelactam precursor and the primary diamine takes place at an elevated temperature and reaction temperatures from about 40° C. to about 300° C. are satisfactory although reaction temperatures from about 100° C. to about 200° C. are preferred. Suitable reaction pressures are those pressures sufficient to maintain the reaction mixture in the liquid phase. Such pressures are generally up to about 20 atmospheres but more often reaction pressures from about 0.8 atmosphere to about 5 atmospheres are employed. During reaction, reactant contact is maintained by conventional methods such as shaking, stirring or refluxing. Subsequent to reaction, an initial reaction product is obtained in the product mixture from which it is obtained by well known procedures such as extraction, precipitation and chromatographic separation.

The initial reaction product resulting from reaction of the spirolactonelactam precursor and the primary diamine is an open chain, acyclic diamide obtained by reaction of each primary amino group with an acidic function of the spirodilactam precursor. In terms of the spirolactonelactam precursors of either formula I or formula II and the primary diamine of formula III, the acyclic initial reaction product is represented by the formula

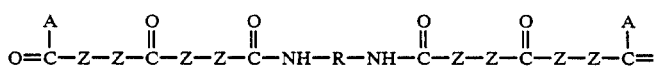

wherein A, Z and R have the previously stated meanings, it being understood that when the spirolactonelactam precursor is a spirolactone the A groups of formula IV will be hydrogen. The nomenclature of the amides of formula IV is difficult because of the complexity thereof. By way of specific illustration, however, from reaction of either 4-oxoheptanedioic acid or 1,6-dioxaspiro[4.4]nonane-2,7-dione and p-phenylenediamine is obtained the diamide is represented by the formula

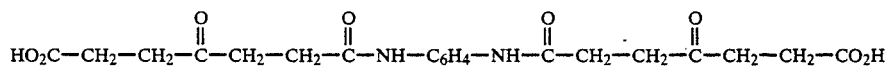

The identity of other illustrative initial reaction products will be apparent from the above formula I, II and III and the discussion of the spirolactonelactam precursor and the primary diamine.

The spirolactonelactam products of the invention are produced from the open chain initial diamide products by a dehydration-cyclization process. Processes which are conventional for removing water from compounds which easily undergo dehydration are suitable. In one modification, the initial reaction diamide product is maintained in a vacuum at an elevated temperature to remove the elements of water from the molecule and thereby cause cyclization. Temperatures from about 150° C. to about 250° C. are suitable and pressures from about 1 atmosphere to about 20 atmosphere are useful. In a second modification the initial diamide product is dissolved in a suitable solvent and water is removed by distillation. Use of a solvent, alone or in combination with other solvents, with which water forms an azeotrope is particularly useful. Such solvents include toluene and ethylbenzene.

The spirodilactonelactam products of the invention are characterized by a divalent linking group, conceptually derived from the primary diamine by loss of the amino groups, which connects two moieties of 1-aza-6-oxaspiro [4.4]nonane-2,7-dione through the spiro ring nitrogen atom. In terms of the spirolactonelactam precursor of formula I or II and the diamine of formula III, the spirolactonelactam products are represented by the formula

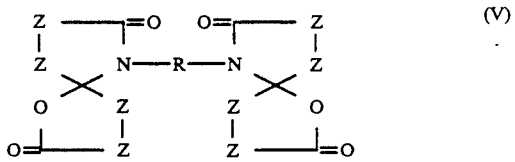

wherein Z and R have the previously stated meanings. The nomenclature of these bis(spirolactonelactam)R products is also difficult because of the complexity of the molecular structure. However, by way of a specific illustration, the product of formula V resulting from dehydrationcyclization of the amide of formula IVa is 1,4-di(1-aza-6-oxaspiro[4.4]-nonane-2,7-dien-1-yl)benzene. The identity of other spirolactonelactam products of formula V will be apparent from consideration of the above formulas I-IV and the accompanying description.

The spirolactonelactam products are useful as precursors of thermoplastic polyamide polymers. If the spirolactonelactams of formula V are reacted with additional primary diamine of the H$_2$N—R—NH$_2$ type employed in the production of the spirolactonelactam, a polyamide of alternating spirodilactam moieties and R moieties will be obtained. Such polyamide polymers are also produced by copending U.S. patent application Ser. No. 254,432, filed Sept. 16, 1988. However, the advantages of the present invention include reacting the spirolactonelactam of formula V with a different primary diamine, i.e., a diamine having a different moiety connecting the two primary amino groups. In such an instance, the resulting polyamide will contain alternating spirodilactam units and units derived from the two primary diamines, e.g., "R" units, and the units derived from the diamines will also alternate within the polymer chain. Such a polyamide polymer containing alternating spirodilactam units and amine residue units in which the units derived from two dissimilar primary diamines cannot easily be produced by the process of Ser. No. 254,432, filed Sept. 16, 1988.

The resulting polyamide polymers are thermoplastic polymers and are processed by methods conventional for thermoplastic materials such as extrusion, injection molding and thermoforming. The polyamide polymers find utility in conventional applications for thermoplastics but are particularly useful as engineering thermoplastics in applications where elevated temperatures are likely to be encountered by virtue of the relatively high glass transition temperatures exhibited by the polyamides. Such applications include the production of containers for food and drink and as base materials for electrical and electronic assemblies.

The invention is further illustrated by the following Illustrative Embodiments which should not be regarded as limiting.

ILLUSTRATIVE EMBODIMENT I

A mixture of 28.15 g (0.142 mole) of di(4-aminophenyl)methane, 48.8 g (0.3125 mole) of 1,6-dioxaspiro[4.4]nonane-1,6-dione and 75 ml of N-methyl-2-pyrrolidone was placed in a 500 ml round bottomed flask equipped with a mechanical stirrer and a condenser and was warmed to 150° C. while being stirred. The mixture was maintained at 150° C. for 12 hours and then cooled and poured into 3.5 liters of water. An oily product and an emulsion were formed. The emulsion was decanted and the oily product was precipitated by addition to methanol. The product, di[4-(6-carboxy-4-oxohexanamido)phenyl]methane was obtained in a 91.2% yield (61.4 g), melting point 158° C. -160° C. The infrared and nuclear magnetic resonance spectra were consistent with this structure.

ILLUSTRATIVE EMBODIMENT II

A 2.2 g sample of the product of Illustrative Embodiment I was heated in a vacuum oven at 190° C. -200° C. for 4 hours. The resulting product, bis[4-(1-aza-6-oxaspiro[4.4]nonane-2,7-dion-1-yl)phenyl]methane, was obtained in greater than 90% yield, melting point 135° C. The infrared and nuclear magnetic resonance spectra of the product were consistent with this structure.

What is claimed is:

1. A bis(spirolactonelactam) compound of the formula

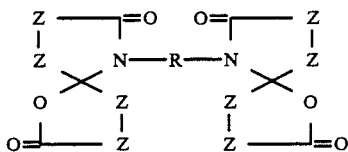

wherein Z independently is $>C(Z')_2$ in which Z' independently is hydrogen, lower alkyl, lower halo or phenyl, or Z is such that two adjacent Z moieties together form an unsubstituted ring Z" of from 5 to 7 ring atoms up to two of which are heteroatoms selected from nitrogen, oxygen or sulfur, with the remaining ring atoms being carbon atoms, two ring carbon atoms of which form a bridge between the carbon atoms connected by the adjacent Z moieties, and R is a divalent radical of up to 30 carbon atoms inclusive, selected from divalent alkylene or divalent arylene of up to 2 aromatic rings inclusive, which, when two rings are present incorporated rings which are fused, connected by a direct valence bound or connected by alkylene of up to 8 carbon atoms inclusive, oxy, thio, sulfonyl, carbonyl, dioxyphenylene, 2,2-di(oxyphenyl)propane, di(oxyphenyl) sulfone or dioxydiphenylene.

2. The compound of claim 1 wherein Z' $>C(Z')_2)_2$ in which Z' is hydrogen or methyl.

3. The compound of claim 2 wherein R is 2 aromatic rings connected by alkylene.

4. The compound of claim 3 wherein R is di(4-phenylene)methane.

5. The compound of claim 4 wherein at least one Z' of each $>C(Z')_2$ is hydrogen.

6. The compound of claim 4 wherein Z' is hydrogen.

7. The compound of claim 1 wherein adjacent Z moieties of each spiro ring are Z".

8. The compound of claim 7 wherein Z" is benzo.

9. The compound of claim 8 wherein R is 2 aromatic rings connected by alkylene.

10. The compound according to claim 9 wherein R is di(4-phenylene)methane.

* * * * *